United States Patent [19]
Langford

[11] Patent Number: 5,207,237
[45] Date of Patent: May 4, 1993

[54] OZONEATED LIQUID SYSTEM

[75] Inventor: Terrence R. Langford, Tucson, Ariz.

[73] Assignee: Kew Import/Export Inc., Tucson, Ariz.

[21] Appl. No.: 954,978

[22] Filed: Sep. 30, 1992

Related U.S. Application Data

[63] Continuation-in-part of Ser. No. 774,047, Oct. 8, 1991, Pat. No. 5,184,633, which is a continuation-in-part of Ser. No. 556,570, Jul. 20, 1990, abandoned.

[51] Int. Cl.$^5$ ................................................ B08B 3/10
[52] U.S. Cl. .................................... 134/102.1; 292/305
[58] Field of Search ............. 134/36, 37, 102.1, 102.2; 261/DIG. 42; 422/28, 29, 30, 33, 113, 116, 186.07, 186.08, 186.10, 186.11, 186.12, 186.14, 292, 294, 295, 305, 296; 210/760; 8/158, 159; 68/3 SS, 13 R

[56] References Cited

U.S. PATENT DOCUMENTS 4,898,679  2/1990  Siegel et al. ................ 210/760 X
5,082,558  1/1992  Burris ...................... 422/186.08 X Primary Examiner—Philip R. Coe
Attorney, Agent, or Firm—Ogram & Teplitz

[57] ABSTRACT

A liquid ozone system in which a liquid bath, preferably of distilled water, is kept in a pressure vessel and gaseous ozone is diffused into the liquid. The ozonenated liquid is then used as a steriliant in a container which is engagable with the pressure vessel. In the preferred embodiment the container and the pressure vessel are chilled to maintain the ozone diffused in the liquid. Excess liquid from the container is communicated to a destruct mechanism such as activated charcoal or discharged into the waste water system.

28 Claims, 6 Drawing Sheets

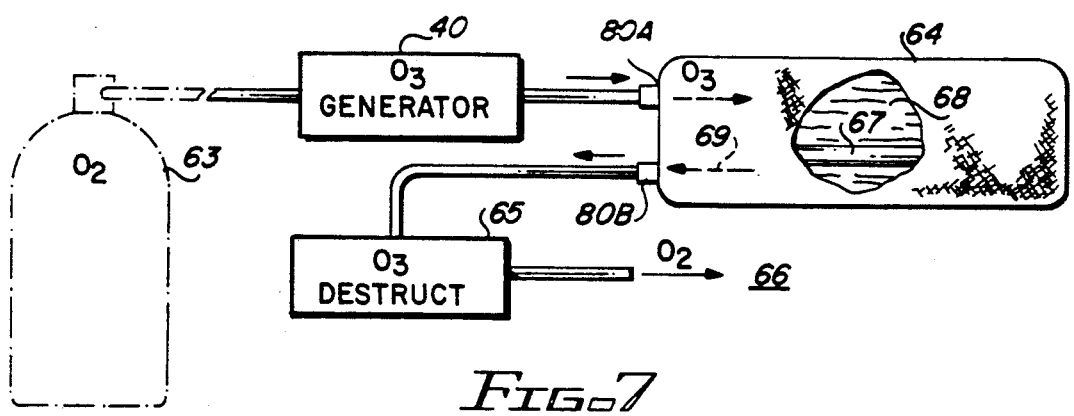
FIG. 7
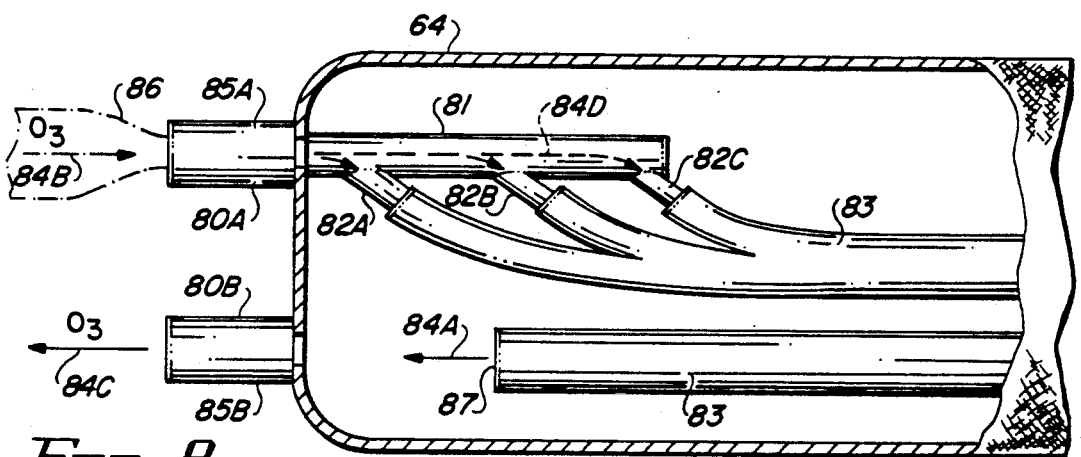
FIG. 8
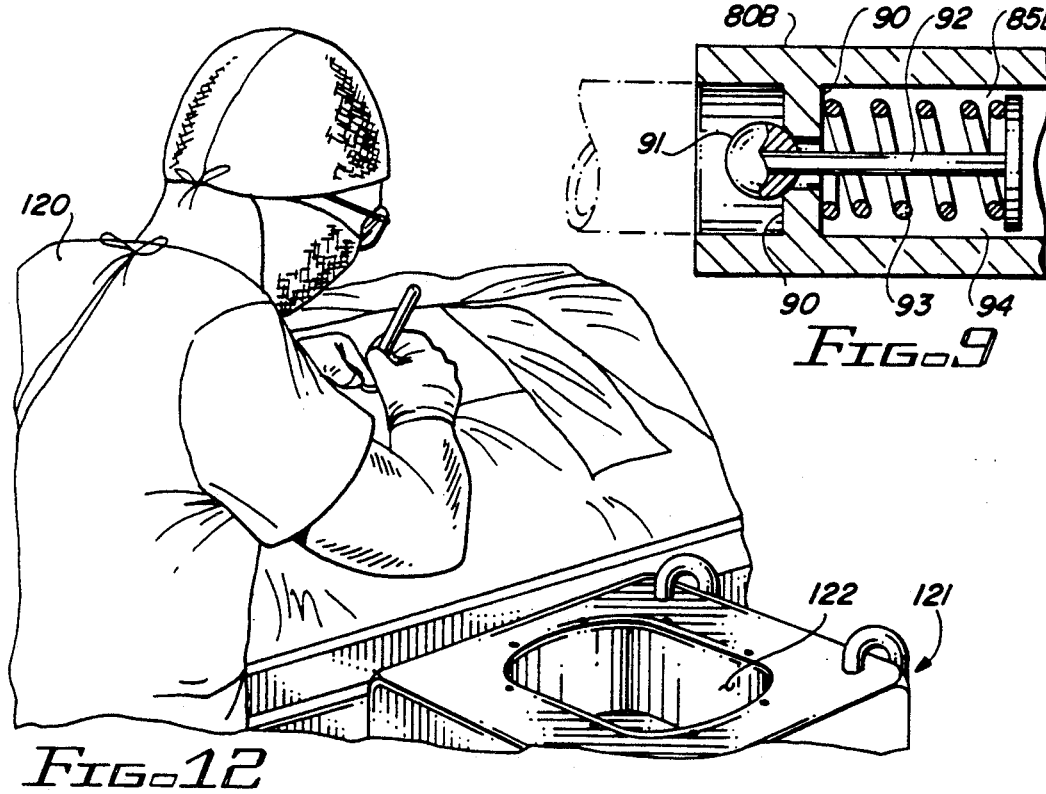
FIG. 9
FIG. 12

OZONEATED LIQUID SYSTEM

This is a continuation-in-part of U.S. patent application Ser. No. 07/774,047, entitled "A Cleansing and Sterilization Mechanism Suitable for Contact Lenses and the Like" filed Oct. 8, 1991, and now U.S. Pat. No. 5,184,633; which was a continuation-in-part of U.S. patent application Ser. No. 07/556,570, entitled "A Contact Lense Device and Method" filed Jul. 20, 1990, and now abandoned.

BACKGROUND OF THE INVENTION

This invention relates generally to sterilizing systems and particularly to sterilizing systems which utilize ozone suspended in a liquid as the sterilizing agent.

Although this invention has tremendous applications to a variety of items to be cleaned including but not limited to, dental tools, surgical instruments, implants, etc., for an understanding of the problems associated with cleansing and sterilization, the following discussion focusses on the cleansing and sterilization of contact lenses.

The success or tragic failure of contact lens wear is ultimately determined by the care and aseptic handling of the lenses. With over seventeen million contact lens wearers in the United States spending two billion dollars on contact lens supplies, a simple one step cleaning and sterilizing process is sought. Both hard and soft lenses currently need daily, or in the case of extended wear contacts, weekly cleaning and antiseptic treatment.

By their very nature, being in close relationship with the wearer for extended periods of time, contact lenses are susceptible to both: buildups of protein and lipids from the wearer; and also from contamination from microorganisms. Either of these, buildup or contamination, can have debilitating affects such as reduced vision, scarring of the eye, and even blindness.

Hydrophilic contact lenses, being soft and composed mainly of water, have made the problem of cleaning even more difficult. Physical pressure on the hydrophilic lense may cause rips; strong disinfectants become lodged within the body of hydrophilic lense itself and then irritate the wearer's eye causing an ulcer.

Without a good cleaning process, both the hard and soft contact lense is susceptible to a wide variety of contaminating microorganisms including: Acanthamoeba, Pseudomonas organisms, *Alcaligenes faecalis*, staph, Aureus, and *Enterobacter aerogenes.*

For a through understanding of the diseases associated with contact lenses, see: "Pseudomonas aeruginosa Contamination of Hydrophilic Contact Lenses and Solutions", by Milauskas, appearing in *Transactions of the American Academy of Ophthalmology and Otology*, vol. 76, March-April 1972, page 511; "Complications Associated with Contact Lens Solutions", by Morgan, appearing in *Ophthalmology AAO*, vol. 86, June 1979, page1107; "The Soft Plastic Contact Lenses", By Dastoor, appearing the *Indian Journal of Ophthalmology*, vol. XXI, on page 25; "Microbiological Evaluation of Soft Contact Lens Disinfecting Solutions" by Houlsby et al., appearing in the *Journal of the American Optometric Association*, vol. 55, Number 3, page 205; and, "Susceptibility of Acanthamoeba to Soft Contact Lense Disinfection Systems", appearing in the *Investigative Ophthalmology & Visual Science*, April 1986, Vol. 27, page 626.

Additionally, the high water content of hydrophilic contact lenses make them more susceptible to the formation of "jelly bump" deposits which are composed primarily of lipids and calcium. These lipid formations are usually long and intermediate chain cholesterol esters and triglycerides which are particularly difficult to remove from a soft lense without damaging the lense. A good review of this problem is "Origin and Composition of Lipid Deposits on Soft Contact Lenses" by Hart et al., and appearing in *Ophthalmology*, April 1986, vol. 93, No. 4, page 495.

The typical method of cleaning, using a saline solution and distilled water approach has not been totally satisfactory. It has been found that this approach does not truly address the contamination problem; indeed, several of the contaminating microorganisms actually thrive in the cleaning environments.

Because of this, the industry has been seeking alternative cleaning approaches which may be used by the wearer, not a laboratory.

One technique proposed is the use of a 3% hydrogen peroxide solution for the cleaning and disinfecting the lenses. The reason for this popularity is that after disinfecting, the hydrogen peroxide is converted into innocuous by-products which are compatible with ocular physiology.

The hydrogen peroxide approach is well described in: "A Comparison of New Hydrogen Peroxide Disinfection Systems" by Krezanoski et al., and appearing in the *Journal of the American Optometric Association*, vol, 59, No. 3, page 193; "Efficacy of Hydrogen Peroxide Disinfection Systems for soft Contact Lenses Contaminated with Fungi", by Penley et al., and appearing in the *CLAO Journal*, January 1985, vol. 11, no. 1, page 65; "Reaction to Hydrogen Peroxide in a Contact-Lens Wearer", by Knopf, appearing the *American Journal of Ophthalmology*, June, 1984, page 796; "Hydrogen Peroxide in Anterior Segment [Physiology: A Literature Review", by Chalmers, appearing in *Optometry & Vision Science*, pages 796; and, "Hydrogen Peroxide Sterilization of Hydrophilic Contact Lenses', by Gasset et al., and appearing in *Arch. Ophthalmology*, vol, 93, June 1975, page 412.

Unfortunately, hydrogen peroxide, at the 3% level or even the 6% level, is incapable of disinfecting some of the hardier microorganisms. Further, hydrogen peroxide does not have noticeable affect upon the "jelly bumps".

Perhaps the most common treatment is the heat method. In this approach the contact lenses are exposed to a temperature of eighty degrees centigrade for a period ten minutes. This approach is more effective than chemicals against microorganisms but the treatment substantially decreases the life of the contact lenses and is usable only with about half of the present contact lenses. Use of this method depends heavily upon the water content and the type of plastic used in the lenses' construction.

Additionally, proteins and other contaminants that are left in the contact lense (buildup) can substantially produce irritation in the eyes of the user.

It is clear from the foregoing that an efficient and through cleaning and sterilizing technique does not exist.

SUMMARY OF THE INVENTION

In the present invention, a liquid bath, preferably of distilled water, is kept in a pressure vessel and gaseous ozone is diffused into the liquid. The ozonenated liquid is then used as a steriliant in a container which is engagable with the pressure vessel. In the preferred embodiment the container and the pressure vessel are chilled to maintain the ozone diffused in the liquid. Excess liquid from the container is communicated to a destruct mechanism such as activated charcoal or discharged into the waste water system.

The invention has applications to a variety of embodiments which are discussed herein.

In the preferred embodiment of the invention, a cleansing and sterilization mechanism is created which is usable on contact lenses, surgical instruments, dental tools, and other items which require regular cleansing and sterilization. Using ozone as the cleansing and sterilization medium, the apparatus provides for added guaranty of operation through the use of feedback mechanism to assure that all the components are working and that the to-be-cleaned items are exposed to the ozone bath for the specified time. Furthermore, the item is capable of communicating, vis phone line, to a central unit which monitors the operation and performance of the mechanism.

Fundamentally the present invention consists of a housing having therein an ozone generator, a pump, and a controller. A container holding the items to be sterilized and cleansed is insertable into the housing. The controller assures that both the pump and ozone generator are operating. Via valves in the container, ozone is directed over the to-be-cleaned items forming an ozone bath. After the proper amount of time has elapsed, the controller either shuts down the pump and ozone generator, or the controller redirects the ozone to another container (depending on the embodiment in use).

The container, with the now sterilized items, is removable from the housing and may be carried with the user or moved to a location where the items will be used (i.e. in an operating theater, moved to the operating table). The items within the container are kept sterile through the use of self-sealing valves which seal when the container is removed from the housing.

Although the present invention relates to a variety of items, the application of cleansing of contact lenses is one of the major applications. Because of this, the following discussion relates to the present invention's application of this field.

An ozone generator creates a bath of ozone and saline. A cage or other suitable arrangement, submerges the contact lenses into this bath for a predetermined amount of time. A timer either deactivates the ozone generator at the proper time or alerts the user so that the contact lense should be removed from the bath.

Ozone was discovered in 1840 by Christian Friedrich Schonbien. Ozone is three oxygen atoms bonded together. Unfortunately, ozone has a very short life, usually about twenty minutes. As the ozone breaks down, its natural by products are pure water and stable oxygen.

It is the off-gas ozone which has created the largest concern for health reasons. Standards for the protection of users range in the 0.10 and 0.12 parts per million range.

Because of ozone's ability to control bacteria and virus microorganisms, ozone has been used since the 1890's to purify water for drinking. More recently, ozone has been used in swimming pools to reduce the dependency on chemical purification.

Production of ozone is typically created by passing air past an ultraviolet light in a sealed chamber. This produces an ozone-rich air which is then pumped into a saline bath.

Sterilization using ozone is effective for all ocular pathogens including viruses, bacteria, fungus, and most importantly amoebae. The time of actual ozone exposure to the contact lenses is less than or equal to the present method of heat or chemical aseptisizing, usually ten minutes.

Ozone is the second most powerful oxidant known. This means that ozone: is a powerful oxidant for pollutants and organic contaminants; and, is an excellent steriliant for microorganisms. When compared to chorine, ozone has an oxidizing potential 50% greater and can destroy bacteria and viruses up to three thousand times faster.

Ozone is also a strong oxidizing agent which causes small suspended particles to coagulate and precipitate away from the contact lenses. This assists in the cleaning of the contact lenses since removed matter is quickly and effectively removed from the proximity of the contact lense.

Two different levels of the present invention are envisioned: the first is a home-use apparatus for the cleaning of a single pair of contact lenses; the second is an eye care practitioner's office apparatus for the production cleaning of multiple contact lenses.

The invention is particularly powerful for the home use application. In this situation, the main part which fails in the cleansing and contact lenses is the user himself. Typically, the user forgets to cleanse the contact lense and then "swears" to his doctor that the cleansing was done religiously.

In certain countries, especially European countries, the responsibility of assuring that the user does clean the contact lense falls upon the physician. Because of this, the physician wants to be sure that i) the user is using the device, and ii) the user will return to the physician regularly for follow-up examinations.

In the preferred embodiment, the present invention accomplishes these objectives by having a prescribed number of "cleanings/sterilizations" logged onto a memory chip. The user is able to use the device only this many times and then must return to the physician to have the use data reestablished. Furthermore, the physician is able to poll the device, via the phone lines, as to the actual number of uses the user has made of the device.

In operation, the preferred embodiment of the invention:

1) The power is turned on to the unit by the user;
2) The on-board computers checks to see if the pump and ozone generator lamp are off;
3) The computer checks to see how many counts are remaining in the memory count-down;
4) Based upon these checks, the computer,
   a) If the count is zero, the computer notifies the via such devices as flashing Light Emitting Diodes (LEDs) and shuts down the operation, or,
   b) If the count is under a predetermined warning level (i.e. 10), then the operator is notified via the LEDs and the ozone generator and pump are activated, or,
   c) If the count is above the warning level, the computer notifies the user via the LEDs and the ozone generator and pump are activated;

5) The computer waits a short period of time (i.e. 300 milliseconds) and checks to see that the pump and light are activated;

6) The computer waits another short period of time (i.e. 1 second) and checks to see if gas flow is detected [note- steps 5 and 6 are safety checks to see if the apparatus is working];

7) After the prescribed amount of time (i.e. 19 minutes) the computer shuts off the ozone generator permitting the pump to continue operation to purge the system; and, 8) After the ozone generator is deactivated, the pump operates a short period (i.e. 1 minute) before the computer deactivates the pump.

Studies conducted have found that using an ozone generator producing 0.02 grams of ozone per hour requires a submersion of 3 minutes for a thorough cleaning.

In an enhanced embodiment, the contact lenses are automatically removed from the ozone bath at the termination of the proper elapsed time and the ozone generator is switched "off". Once removed from the ozone bath, the contact lenses are rinsed with a saline solution, permitting any ozone which may have impregnated the lenses, particularly hydrophilic contact lenses, to break down into harmless elements.

The preferred embodiment of the present invention utilizes an ozone generator producing from 0.01 grams to 1 gram of ozone per hour. This is the preferred level since it reduces any health dangers which might occur form air-suspended off-gassed ozone. Those of ordinary skill in the art readily recognize how to construct an ozone generator having this capability.

Those of ordinary skill in the art acknowledge the use of two procedures to produce ozone: ultraviolet radiation; and, corona discharge.

Most ozone generators currently use ultraviolet radiation. These are usually the lowest cost ozone generators on a per unit basis. This decrease in cost is due to the fact that the air does not go through an initial drying process.

Newer units being produced utilize a corona discharge technique which dry the air before charging the air with ozone. This drying permits the corona discharge apparatus to produce a higher ozone concentration.

For minimal expenditures of electrical energy, ozone normally is produced from dried air (−60 degrees fahrenheit dew point) in concentrations of one to two percent and from dry oxygen in concentrations of two to four percent. More than eighty percent of the electrical energy applied to the electric discharge field is converted to heat and, if this is not quickly removed from the cell, the heat causes rapid decomposition of the ozone back to oxygen. The rate of this reverse reaction increases rapidly above thirty-five degrees centigrade. Proper cooling of the ozone generator cells is critical to maintaining consistent yields of ozone.

For the second type of apparatus, that of a production cleaning device in an eye care practitioner's office, multiple containers are used for cleaning several sets of contact lenses simultaneously (or alternatively for cleaning several sets of surgical instruments or dental tools). In this application the controller also detects when a container is placed with a slot in the housing and then operates on the multiple containers on a first come-first served approach.

If the ozone generator is sufficiently large, then multiple containers may be cleansed/sterilized simultaneously.

For both versions, the air flow is generated by a bellows type low pressure pump. Those of ordinary skill in the art readily recognize other pumps which will serve this function.

Also, for all the applications, the containers are automatically sealed upon removal from the housing. This is accomplished by any of several mechanisms well known to those in the art.

This feature, of sealing upon removal, permits the transportation of the contact lense, or other such device, without fear of contamination. In the preferred embodiment, when the lid to the container is opened, this opening shifts and indicia so that, later, the user is able to determined that the container has been opened and that the items are no longer considered sterile.

In the production cleaning embodiment, the ozone generator preferably produces 0.01 grams to 5 grams of ozone per hour.

Studies have determined that ozone levels of as low as 0.001 grams per hours are effective and that 0.006 grams per hour is an efficient balance between sterilizing affect and energy demands for the generation of the ozone.

One important attribute of the present invention is its ability to provide a variety of levels of "cleaning". It has been found that by varying the amount of ozone and the amount of elapsed time of exposure, contact lenses may be disinfected, asepticized, or even sterilized. None of the current state of the art devices can achieve these results without damaging the contact lenses or producing harmful effects to the eye.

A plethora of related inventions are also involved with the core preferred embodiment. These inventions expand upon the capability and functionality of the preferred invention.

In a variety of situations, the need exists for a "dry" ozone stream. Many instruments and devices either rust or corrode if exposed to a humid or wet environment. To this end, a recognition of Henry's Law where at sufficiently high dilution in a liquid solution, the fugacity of a nondissociating solute becomes proportional to its concentration is important; hence, through the proper manipulation of temperature and pressure, and life of ozone, whether in a liquid such as water or in a gaseous steam, is prolonged.

In the preferred embodiment of a dry ozone stream, a pressurized source of oxygen communicates with the ozone generator. This pressurized oxygen is "dry" in that no water vapor is present. The ozone generator creates ozone from some of the oxygen and communicates an ozone/oxygen gaseous stream. The stream is ideal for treatment of surgical instruments (dental and medical instruments) which would degrade if water was present.

One particularly useful aspect of the present invention is an adapter which is used to communicate the ozone from the ozone generator into a hollow tubing. Within the medical industry, a variety of tubes are used for such applications a gastroscopy, colonoscopy, or other such endoscopy examinations. These tubes are generally hollow with two or more openings into which tools for physician viewing or treatment is inserted and communicated to the area of concern. Once used, these tools are contaminated and must be either sterilized or discarded. Sterilization of these tubes is particularly difficult since the tubes are destroyed with intense heat (eliminating the autoclave as a sterilizing mechanism) and chemical treatment does not always probe into every crevice within the tube, leaving contaminated pockets within the tubing.

In the present invention, an adapter is used to directly communicate ozone from the inlet of the container to all but one of the openings in the tube.

As example, assume there are N (N being an integer greater than one) openings in the tube. The adapter communicates with all of the openings except for one of them. Ozone therefore is passed into the tube in such a manner that it must flow through all areas of the tube before it finally escapes from the one opening still open. The ozone which finally passes from the tubing easily sterilizes the outside of the tubing and all portions of the tubing is sterilized since all possible pockets are eliminated.

This aspect of the invention creates a device which is able to effectively sterilize tubing. Those of ordinary skill in the art readily recognize that an adapter is also effective for sterilizing any hollow article having openings. This would include endoscope handles and other non-tubularly shaped articles.

Although the preferred embodiment utilizes rigid containers in its application, flexible bags are also used. The flexible bags are constructed of a material which is impermeable to contamination and have two ports, an inlet port and an outlet port. In the preferred embodiment, each port is equipped with a valve which permits attachment/detachment between either the ozone generator or an ozone destruct mechanism. Each valve also automatically seals upon detachment.

Additionally, in the preferred embodiment, the valves are pressure activated. The inlet port is opened only when pressure from the ozone generator exceeds a preselected limit. This keeps the contents of the flexible bag sterile until ozone is present.

In a like manner, the outlet port is opened when pressure within the bag exceeds a preselected level. This permits the bag to swell to a point and then release the gas. The induced pressure within the bag keeps the ozone gas under pressure so as to prolong the life of the ozone in the gaseous state or if suspended in a liquid.

In an alternative flexible bag, the bag is equipped with a single opening into which the to-be-sterilized items are placed. A "lid" arrangement is secured to the single opening through a screw-type action. The "lid" has two openings which are selectively open/closed the sterilizing unit. These two openings act as an inlet and an outlet port.

Note that when a flexible bag is used, either an ozone laden gas or an ozone laden liquid is usable as the sterilizing agent. In either case, gas or liquid, the steriliant is passed through the bag and then through the exit port.

Once the sterilization process is completed, the operator removes the bag from the ozone generator and the ozone destruct mechanism and then applies manual pressure on the bag. This "squeezing" of the bag forces excess ozone from the bag through the outlet port's pressure activated valve. In this manner, the bag is shrunk for storage and yet the sterile integrity of the bag's interior is maintained.

An adapter, as discussed above, is also usable by connection to the interior portion of the inlet port. This permits hollow tubes and articles i.e. endoscope handles) to be effectively sterilized within the flexible bag.

Although the use of dry ozone gas is preferred in certain situations, a liquid ozonizated bath is also applicable to certain situations. The present invention provides for an efficient method and apparatus to create this ozonizated bath which is designed to optimize the life and effectiveness of the ozone.

A liquid, such as distilled water, is placed in a pressurized reservoir and ozone gas, as described before, is pumped into the reservoir. Excess gas is vented to keep the reservoir at a preselected pressure level. The ozone gas is diffused into the liquid either directly or through a diffuser mechanism well known to those of ordinary skill in the art. Optionally, the reservoir is also chilled to optimize the suspension of the ozone within the liquid.

One the ozonizated liquid is created, it is usable in any of the applications already discussed. The ozonenated liquid is pumped or released into a container having a material to be sterilized and the excess liquid, together with any debris, is carried to an ozone destruct mechanism such as activated charcoal.

The waste liquid and debris is sterile so it may be disposed of safely through traditional waste water systems such as sewer systems.

This embodiment is particularly useful for the sterilization of materials where a liquid bathing action is preferred due to added contact, agitation for physical removal of contaminates, or for the water's inherit cleansing action.

Agitating of the liquid medium is beneficial and is accomplished through a variety of methods well known to those in the art. Mechanical agitation forces the water to move against the item and thereby remove debris; sonic agitation also dislodges the debris and also forces the suspended ozone gas into a "fiz-type" of state which further encourages the dislodging of debris.

This embodiment of the invention is particularly useful for the cleansing and sterilization of endoscopes which have biological debris attached to them. As example, the cleansing of material from a laparoscope is greatly facilitated by the agitation action.

In this regard, one aspect of the present invention relates to the treatment of flexible, usually woven, materials which have become contaminated with biological wastes. One such application is generated in the medical field associated generally with surgeries; those of ordinary skill in the art readily recognize various other applications which generate a similar type of waste.

In the surgical application, a large number of sponges, bandages, wipes, and the like are generated. These biologically contaminated waster materials are discarded into a receptacle called a "red bag". The red bags are collected from the various points within the hospital and are typically incinerated. The steps between the operating room and final incineration requires numerous handling by humans which increases the potential of infection to these handlers. Additionally, many hospitals are not licensed to have incinerators.

The present invention is a self-contained mechanism which is "wheeled" into the operating room (or other suitable place) next to the surgeon. As with the red bag, the surgeon disposes of the waste by throwing it into the self-contained mechanism's drum's top opening. When the operation is completed, the top of the drum is sealed and the mechanism is "wheeled " into another room. The mechanism is attached to electrical power, a liquid source, and a waste water disposal port. The preferred liquid in this application is distilled water, but, those of ordinary skill in the art readily recognize various other liquids which serve this function.

Once so connected, the mechanism is started. Note that at no time, other than the surgeon, is the waste handled by any human.

In operation, the mechanism creates an ozonenated bath as discussed before and mixes this with a detergent which is pumped into the drum. Through an agitating mechanism, the contents of waste, ozonenated liquid, and detergent, are mixed and agitated so that an initial bathing/sterilization action is performed. In the preferred embodiment, the drum is both pressurized and chilled to increase the life of the ozone.

In this embodiment, water is used to create a bath. This water is either distilled or is filtered so that a maximum life of the ozone gas is obtained. Those of ordinary skill in the art readily recognize other medium which can be used in this context.

Although the embodiment above discusses the use of detergent with an ozone bath, ozone is also useful to degrade detergent. As such, in one embodiment of the invention, the detergent with water (without ozone) is used as an initial washing action followed by the addition of an ozone bath. This structure provides for not only the cleansing and sterilization, but also a breakdown of the detergent rendering it less harmful for the environment.

Once the initial bath is completed, the residue and liquid are removed from the drum, either through simple pumping action or in combination with a spinning action of the drum. Note that the residue is sterilized and can be discharged without concern for biological contamination. Further, the ozone tends to break down the detergent so that it too does not pose any environmental threats.

Another bath of ozonenated liquid is performed on the waste fabrics in the drum before the waste is acceptable for disposal, or in certain situations, reuse.

This arrangement performs a complete sterilization of the waste material without endangering human operators by requiring any additional handling of The invention, together with various embodiments thereof will be more fully described by the following drawings and their accompanying descriptions.

DRAWINGS IN BRIEF

FIG. 7 is a block diagram of the dry ozone aspect of the present invention.

FIG. 8 is a cutaway view of a flexible bag embodiment of the present invention incorporating an adapter.

FIG. 9 is a close-up cut-away view of the preferred pressure release valve as is used in the flexible bag embodiment.

FIG. 12 is a perspective view of the self-contained mechanism showing its application in a surgical application.

DRAWINGS IN DETAIL

Figure 1:
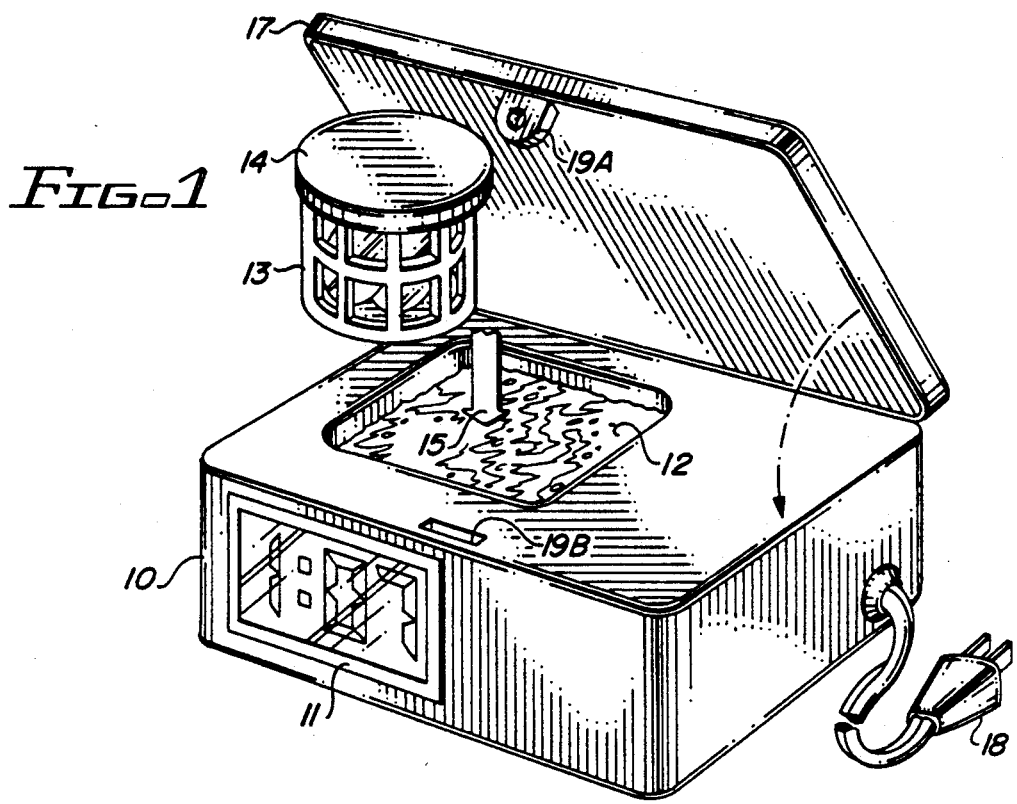
FIG. 1 is a perspective view of a personal use embodiment of the invention.

FIG. 1 is a perspective view of a personal use embodiment of the invention. This embodiment is intended to be used by the contact wearer to periodically clean and disinfect their own contact lenses at home.

Contact lense cleaner 10 receives its power via electrical cord 18 which utilizes household electrical current. This electrical current is used to power clock 11 and the ozone generator (not shown). Clock 11 is a countdown type of clock showing the remaining time necessary for proper cleaning the contact lenses.

The contact lenses are placed in cage 13. To facilitate easy placement of the lenses within cage 13, removable top 14 permits access to the interior portion of cage 13. Cage 13, once the contact lenses are placed therein, is lowered, as illustrated by arrow 15, into basin 12 (having saline therein) and lid 17 is closed, as illustrated by arrow 16.

The closing of lid 17 causes latch 19A to enter receptacle 19B which signals clock 11 that the contact lenses are suitable placed within basin 12. Clock 11 then activates the ozone generator (not shown) to create a bath of ozone and saline within basin 12.

When the selected amount of time has elapsed, clock 11 deactivates the ozone generator and releases lid 17 by latch 19a. The raising of the lid signals the user that the contact lenses are clean and ready for rinsing and use.

In one embodiment of this invention, cage 13 is removable and has a protrusion which supports it above basin 12. This permits the enclosed contact lenses to drip dry and also provide a time lapse for any absorbed ozone to convert to its benign by-products before the user again places the contact lenses within their eyes.

It has been found that through control of the amount of ozone and the amount of time of exposure, contact lenses may not only be cleaned but either disinfected, asepticized, or even sterilized. Control of these factors, amount of ozone and elapsed time, depends upon the manufacturer and user to obtain the desired results.

Figure 2:
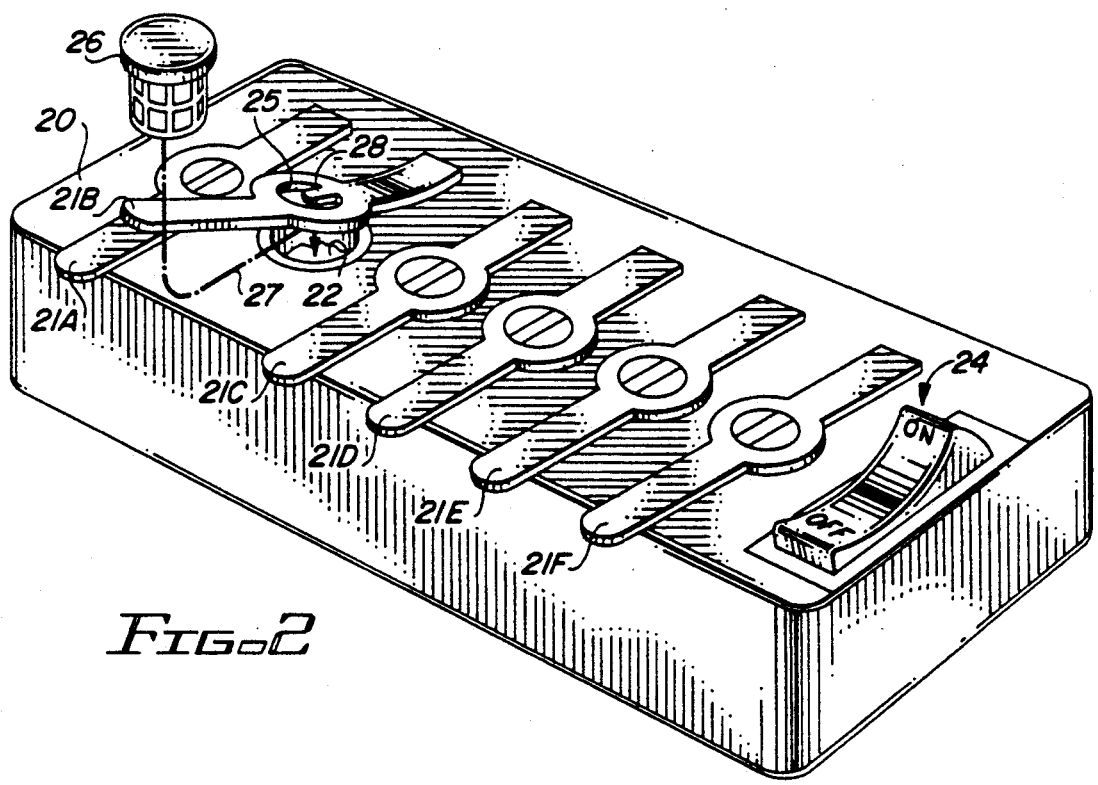
FIG. 2 is a perspective view of a production use embodiment of the invention.

FIG. 2 illustrates an embodiment of the invention for production cleaning. This embodiment is wired into the electrical current of the shop and is activated by a simple on/off switch 24.

Once activated, the bath of ozone and saline contained within unit 20 is created and is constantly fed ozone until the work shift is completed or when the task is completed.

A plurality of holders (21A, 21B, 21C, 21D, 21E, and 21F) are used to clean contact lenses in parallel. Each holder, such as holder 21A, maintains the cage holding the contact lenses in the bath. When the appropriate time has elapsed, the holder raises the cage from the bath.

In this example, holders 21A, 21C, 21D, 21E, and 21F all have cages (such as cage 23 for holder 21A) emersed in the bath. Holder 21B has raised indicating to the operator that cage 26 much have its existing contact lenses removed and another set secured therein.

Once the unclean contact lenses are secured within cage 26, the cage is placed in orifice 25 on holder 21B as indicated by arrow 27. Keeper 28 secures cage 26 in position; the handle of holder 21B is then pushed down forcing secured cage 26 into bath 22.

Keeper 28 is used in this embodiment to secure cage 26 within holder 21B. In another embodiment of the invention, keeper 28 is timed controlled to prevent removal of cage 26 before an alotted amount of time has elapsed for proper drying of the contact lenses.

Those of ordinary skill in the art readily recognize various mechanisms which will work as timing devices for holders 21A, 21B, etc. such as: electronic clocks linked to the holder; spring timed mechanism; and the like.

This embodiment of the invention also illustrates the mechanism which may be used for the personal cleaning apparatus. A mechanism with a single holder is suitable for use by a single user.

Figure 3:
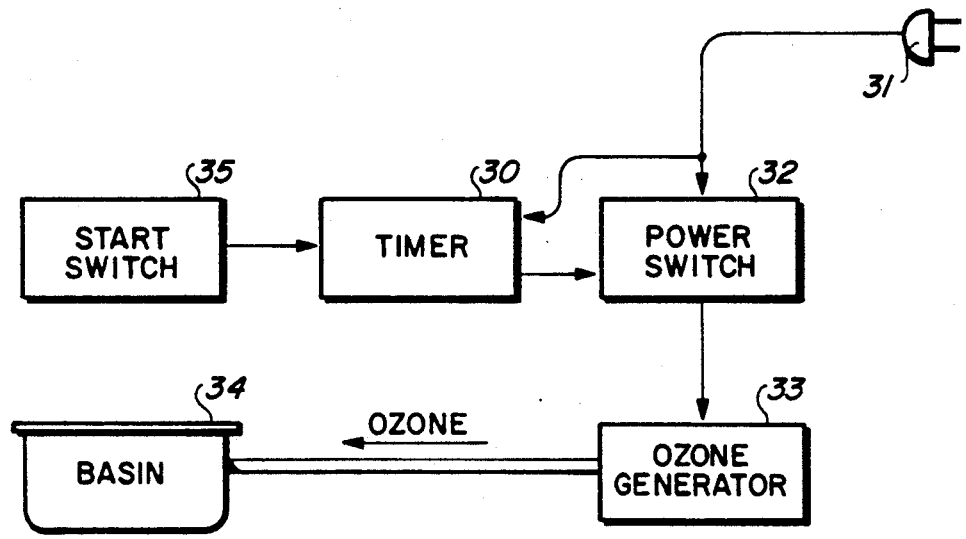
FIG. 3 is a block diagram illustrating the operation of a personal use embodiment of the invention.

FIG. 3 is a block diagram of the operation of an embodiment of the invention. Electrical power is supplied via plug 31 to power switch 32 and timer 30.

Start switch 35 informs timer 30 when the cage holding the contact lenses is properly positioned. Start switch 35 may be a variety of switches well known in the art including the latch switch first illustrated in FIG. 1, a manually operated switch, or any other well known to those in the art.

Once start switch 35 is activated, timer 30, activates ozone generator 33 via power switch 32. Ozone generator provides ozone to basin 34, with saline therein, until such time as timer 30 deactivates the ozone generator 33 by denying electrical power through power switch 32.

It is clear from the foregoing that in this embodiment of the invention, timer 30 acts as a controller for the entire operation of the mechanism.

Figure 4:
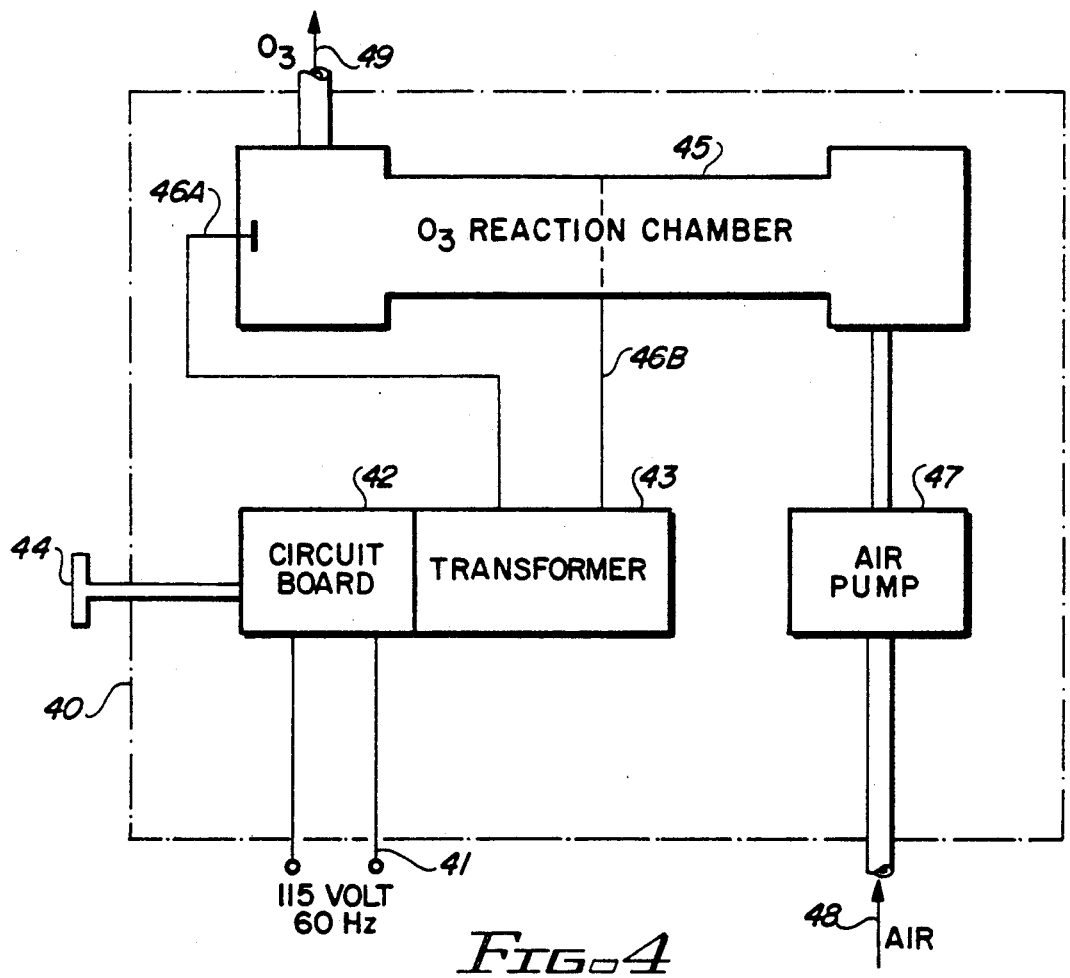
FIG. 4 is a block diagram of the preferred embodiment of the ozone generator.

FIG. 4 is a block diagram of the preferred ozone generator for the invention. Ozone generator 40 receives standard electrical energy 41 being 115 volts at 60 hertz. This electrical energy passes through circuit board 42 and is modified to drive transformer 43 at the prescribed rate as determined by operator adjustment knob 44. Utilizing the operator adjustment know 44, the operator is able to vary the concentration of ozone being produced by ozone generator 40.

Leads from transformer 43 feed a cathode 46A and anode 46B positioned within the ozone reaction chamber 45. Ozone reaction chamber 45 is preferably constructed of stainless steel and has a glass dielectric therein.

Air pump 47 draws in outside air 48 into the system and through ozone reaction chamber 45 producing a flow of ozone 49.

Those of ordinary skill in the art readily recognize alterations which may be made of the present layout to permit this embodiment to be utilized in a variety of settings and for a variety of ozone demands.

Figure 5:
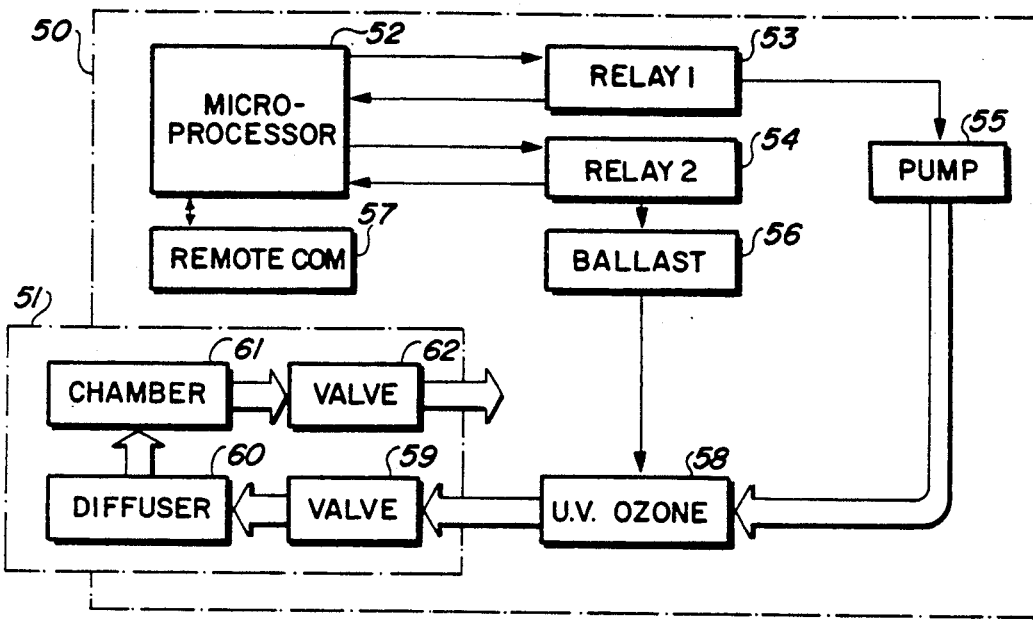
FIG. 5 is a block diagram illustrating the interaction of the components for the preferred embodiment of the contact lense cleanser/sterilizer.

FIG. 5 is a block diagram illustrating the interaction of the components for the preferred embodiment of the contact lense cleanser/sterilizer.

Main unit 50 receives electrical power (not shown) via a typical house outlet of 110 volt. Microcomputer 52 acts as a controller for the entire unit. By activating relay 1, microcomputer 52 is able to activate pump 55; by activating relay 54, microcomputer is able to activate ballast 56 which energizes the Ultraviolet ozone generator 58.

Air flow from pump 55 is passed through the ozone generator 58 and ozone is created. The ozonizated air flow passes into container 51 via valve 59. Ozone bubbles within the air flow are broken into small bubbles via diffuser 60. Diffusion of the ozone increases the surface area of the ozone and thereby increases the overall effectiveness.

The diffused ozone air flow passes through chamber 61 where the items to-be-cleaned are placed. Finally, the ozone air flow is exhausted via valve 62.

Both valve 59 and valve 62 seal when container 51 is removed from housing 50. Container 51 keeps the contact lenses, or other items, sterile until container 51 is opened.

Microcomputer 52 is able to communicate with a remote computer (not shown) via remote communication link 57. In the preferred embodiment, this remote communication link is a modem type device although those of ordinary skill in the art readily recognize various other mechanism which will serve this purpose.

Memory, located in this embodiment within microcomputer 52, is nonvolatile permitting a constant upgrade of the operational data and also of the time parameters and usage of the device. This information is easily communicated via the remote communication link 57.

Additionally, remote communication 57 permits a remote computer, such as in a physician's office, to reset the device permitting the operator to use the device once his allotted amount of uses has been completed. This practice assures the physician that the user is actually using the device and also forces the user to come in for scheduled reexamination to assure that the contact lense is not causing some unforeseen damage to the eye.

Microcomputer 52 is able to monitor, via sensors (not shown) the operation of pump 55, ballast 56, ozone generator 58, and that container 51 is securely placed within housing 50. So long as everything is operating within specifications, microcomputer operates the assemblage until the predetermined amount of time has elapsed.

Should one of the components malfunction, then microcomputer terminates operation and informs the operator of the aborted operation.

Should the application require, a filter is added to valve 62 to trap excess ozone from entering the atmosphere.

Figure 6:
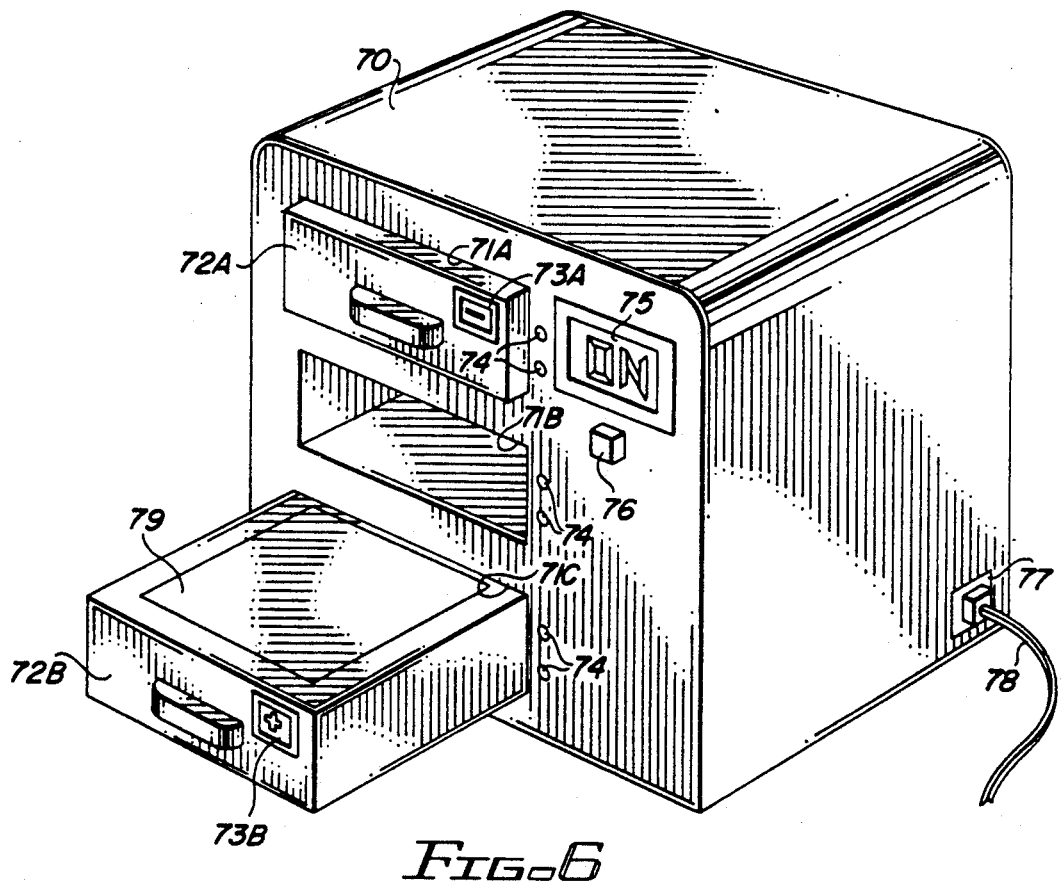
FIG. 6 is a perspective view of an embodiment of the invention utilizing multiple container capability.
Figure 10A:
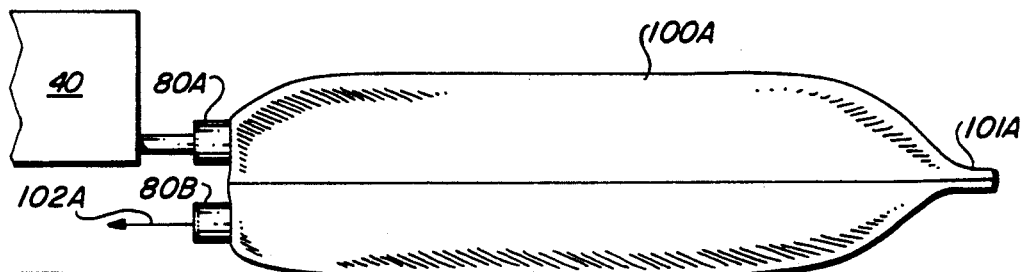
FIGS. 10A-10E are side views of a flexible bag embodiment in use.
Figure 10B:
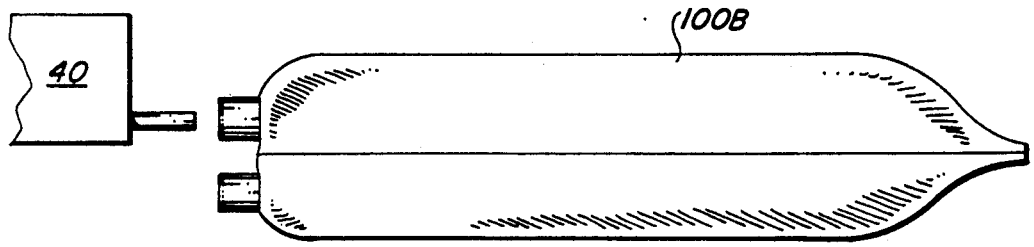
Figure 10C:
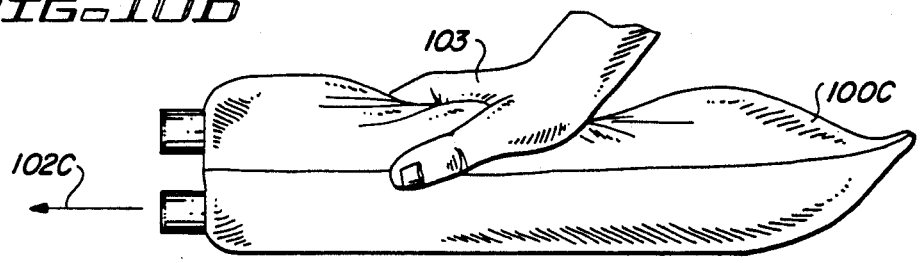
Figure 10D:
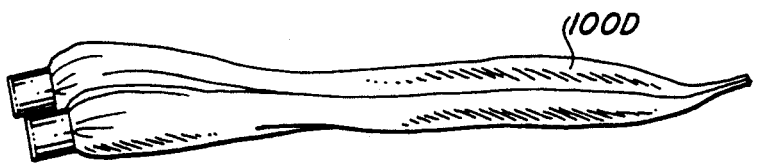
Figure 10E:
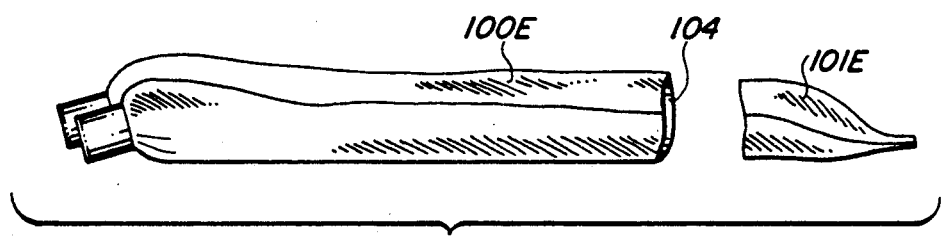

FIG. 6 is a perspective view of an embodiment of the invention utilizing multiple container capability.

Housing 70 contains multiple slots 71A, 71B, and 71C. Although this embodiment illustrates three slots, those of ordinary skill in the art readily recognize that any number of slots is possible.

Into these slots are inserted containers 72A and 72B. Note that slot 71B is empty at the present time. In this embodiment, once a container has had its contents sterilized, it may be removed and stored without contaminating the contents since the valves (not shown) are self-sealing and lid 79 is also sealed.

As an added contamination safeguard, indicators 73A and 73B are used to indicate if the contents are sterile or not. The microcomputer (not shown) moves indicator 73B to a "+" indicating that the sterilization process in complete; opening of the lid moves indicate to a "−" (as shown in 73A. In this fashion, a sterile container is easily identified.

Status display 75 is used by the microcomputer to communicate with the operator. Switch 76 permits the operator to activate/deactivate the device.

Communication with remote computers is facilitated via modular jack 77 and phone line 78.

FIG. 7 is a block diagram of the dry ozone aspect of the present invention.

Oxygen gas is supplied from a pressure vessel, illustrated in this example as a pressurized bottle 63, to ozone generator 40. Ozone generator 40 converts some of the oxygen gas into ozone resulting in an oxygen/ozone mixture being delivered to flexible bag 64.

Flexible bag 64 contains an instrument 67 therein which is exposed to the oxygen/ozone gas mixture 68 which circulates within flexible bag 64 and then exits, 69, to ozone destruction mechanism 65 before being exhausted into the atmosphere 66.

Ozone destruction mechanism 65 is any one of many well known to those of ordinary skill in the art including, but not limited to, activated charcoal filters.

In this embodiment, the dry ozone gas so generated is particularly useful for metal instruments and for sharpened instruments where heat would dull their edge.

FIG. 8 is a cutaway view of a flexible bag embodiment of the present invention incorporating an adapter.

Flexible bag 64, in this embodiment, is constructed of two sheets of impermeable material, well known to those of ordinary skill in the art, which are sealed around the periphery. An inlet port 80A and an outlet port 80B permit the introduction and exhausting, respectively, of ozone gas. Connectors, such as connector 86, press into and seal with ports, permitting ozone to be communicated, as illustrated by arrow 84B.

The ozone stream passes valve 85A, and in this embodiment, pass into adapter 81. Adapter 81 attaches to the interior side of input port 80A. In this illustration, adapter 81 has three connectors, 82A, 82B, and 82C, which connect to three openings in tube 83. Ozone gas is thus forced into each opening to pass through the entirely of the tube 83 and finally exit from end 87 as illustrated by arrow 84A. In this manner, the ozone fully sterilizes the interior of tube 83 and the ozone then proceeds to sterilize the exterior of tubing 83 once it exits.

When pressure within the flexible bag 64 reaches a selected level, valve 85B of outlet port 80B opens permitting the gas to escape as illustrated by arrow 84C. Valve 85B is important in that it maintains pressure within flexible bag 64 so as to increase the life and effectiveness of the ozone, and also assures that no inward flow is permitted through the outlet port 80B; this latter attribute prevents contamination of the interior of bag 64.

As those of ordinary skill int he art recognize, the flexible bag, configured with the inlet port and outlet port with associated valves, is applicable to a variety of situations where a steriliant, other than ozone, is used.

In an alternative flexible bag, the bag is equipped with a single opening into which the to-be-sterilized items are placed. A "lid" arrangement is secured to the single opening through a screw-type action. The "lid" has two openings which are selectively open/closed the sterilizing unit. These two openings act as an inlet and an outlet port.

In this embodiment, the valves are not pressure activated but seal upon removal of the bag from the ozone generator.

Note that when a flexible bag is used, either an ozone laden gas or an ozone laden liquid is usable as the sterilizing agent. In either case, gas or liquid, the steriliant is passed through the bag and then through the exit port.

FIG. 9 is a close-up cut-away view of the preferred pressure release valve as is used in the flexible bag embodiment. Those of ordinary skill in the art readily recognize various other valves which are useful in this application including a shut-off valve found in various applications.

Although FIG. 9 illustrates an outlet port valve, those of ordinary skill in the art readily recognize that by simply turning the valve to face the other direction, the same valve is useable as the inlet port's valve.

Inlet port 80B is constructed to have shoulders 90 imposed therein. Ball 91 seals the opening between shoulders 90 and is retained by post 92 and spring 93. As pressure within chamber 94, fed from the flexible bag-not shown in this figure, increases, the force exerted on ball 91 increases until such time that the pressure overcomes the force from spring 93 permitting some internal gas to escape until such time that the pressure is reduced to a point where spring 93 may again reseal the valve.

Through proper adjustment in the engineering of spring 93 and the length of post 92, the level of pressure necessary to open the ball 91/shoulder 90 combination is adjusted.

This valve permits the controlled exhausting of gas without any reverse flow which would cause contamination within the flexible bag.

An alternative port arrangement doesn't use pressurized valves but instead relies upon valves which are automatically opening by the ozone generator after ozone steriliant begins to flow and which closes the valves prior to the shut-down of the ozone steriliant. Those of ordinary skill in the art readily recognize various mechanisms which accomplish this objective.

FIGS. 10A–10E are side views of a flexible bag embodiment in practical use.

As discussed earlier, ozone generator 40 passes ozone via input port 80A into the flexible bag causing it to inflate, 100A. One end of the flexible bag is sealed, 101A. Sealing of the bag is accomplished through a variety of methods well known to those of ordinary skill in the art, including but not limited to, the formation of a resealing mechanism in which a bead on one edge is securable to a bead locking mechanism. In this embodiment, the sealing is through heat melding of the sides of the flexible bag to each other.

Flexible bag 100B is detached from the ozone generator 40 and is deflated through manual pressure 103. Manual pressure 103 forces gas 102C through the outlet port of bag 100C so that the bag becomes smaller 100D and easier to store and move. Flexible bag 100D is stored and easily handled without losing the sterile integrity of the bag.

When the operator is ready to use the contents of bag 100D, the end 101E of the bag 100E is cut off, 101E, resulting in opening 104 from which the sterile instruments are removed. In this manner, the instruments are kept sterile until such time that they are used.

Should the user wish to reuse bag 100E, then by simply placing the contaminated instruments into the bag via opening 104 and resealing the opening, through a heat sealing operation, the bag is reused several times.

Figure 11:
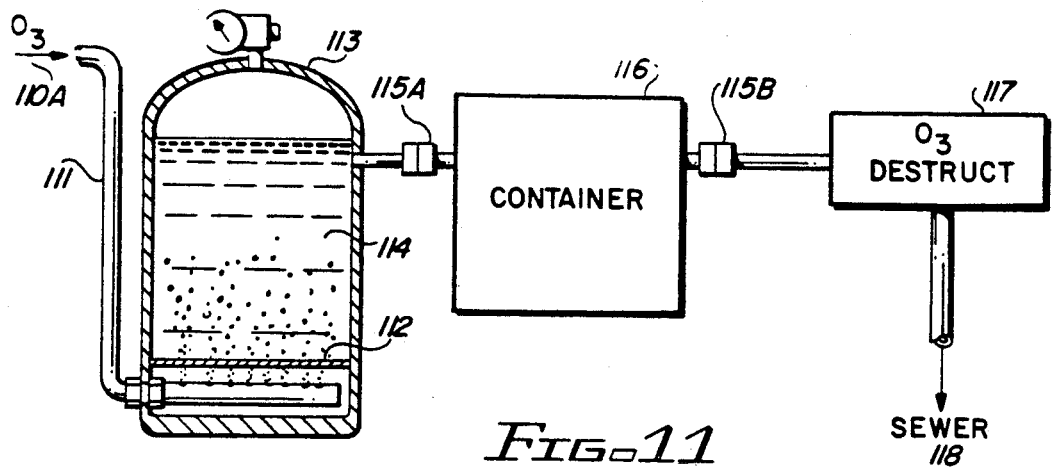
FIG. 11 is a block diagram of the creation of ozonenated liquid and its use in sterilization.

FIG. 11 is a block diagram of the creation of ozonenated liquid and its use in sterilization.

In many situations, there is a need for a liquid sterilizing agent. The embodiment of FIG. 11 creates such a source of ozone. By applying ozone gas under pressure 110A to pipe 111, the ozone is forced into bath 114 within reservoir 113. In this embodiment, reservoir 113 is sealed for pressurization and is chilled (not shown) to prolong the life of the suspended ozone within the water. Also, in this embodiment, distilled water is used as the liquid medium, but those of ordinary skill in the art readily recognize various other liquids which will work in this application.

The gaseous ozone is passed through diffuser 112 into the water and is suspended therein. Excess gas is vented so that pressure within the reservoir is kept within tolerances of the container.

Once the water has been fully charged with ozone, the ozonenated water is passed through connect valve 115A to container 116 for sterilization of the contents. Connect valve 115B permits container 116 to be removed from the ozone destruct mechanism 117.

Spent liquid from the ozone destruct mechanism 117 is discharged to the sewer 118.

FIG. 12 is a perspective view of the self-contained mechanism showing its application in a surgical application.

This embodiment has applications to operating rooms, dressing stations, maternity rooms, and delivery rooms. Anywhere there is a large volume of biologically contaminated material generated, this embodiment is useful.

Within the operating theater, a large amount of biologically contaminated waste is generated which must be either destroyed or sanitized. This self-contained mechanism permits the surgeon 120 to toss such contaminated material directly into a drum within mechanism 121 via top opening 122.

The self-contained mechanism is later wheeled into a room for treatment.

Figure 13:
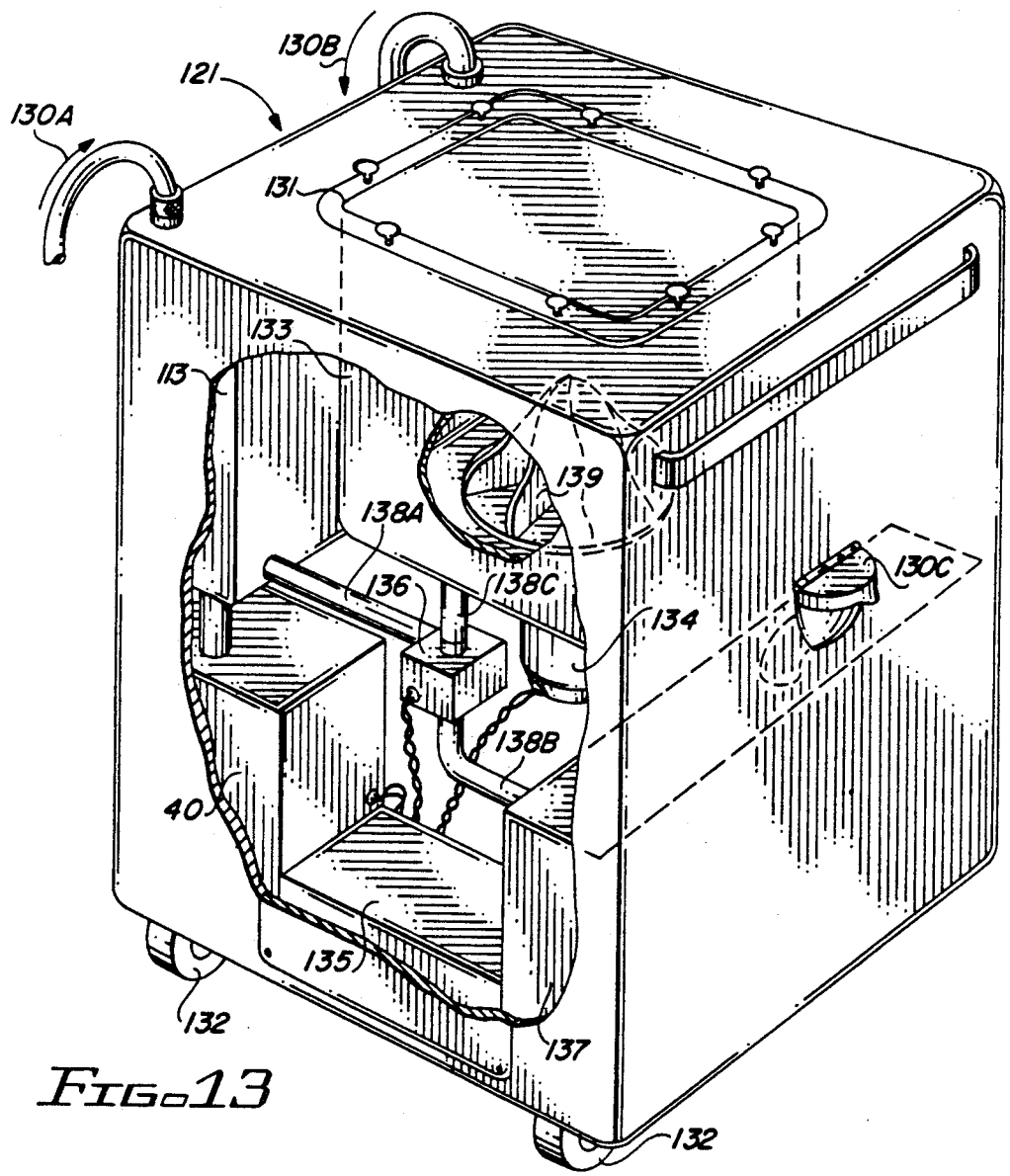
FIG. 13 is a cut-away view of the preferred self-contained mechanism showing the components thereof.

FIG. 13 is a cut-away view of the preferred self-contained mechanism showing the components thereof.

Container 121 has its drum 133 sealed via lid 131. Lid 131 helps to maintain pressurization of drum 133. Note, no human handling of the contaminated material is required. Mechanism 121 is easily moved from the operating room to another location via wheels 132.

Once so sealed, mechanism 121 is attached to a water source 130A, a waste disposal source 130B, and an electrical source (not shown). Activation of the mechanism causes water reservoir 113 to be charged with ozone from ozone generator 40. In the preferred embodiment, reservoir 113 is pressurized and chilled to a selected temperature.

The operator fills a detergent reservoir 137 via fill hole 130C.

In the preferred embodiment, waste source 130A flows though filter 140 which removes suspended particles and probides a relatively pure source of water to the mechanism 121. Filter 140 is preferrably constructed of a coconut carbon wilth silver impregnated carbon with cation and anion resins so that maximum filtration is obtained.

Computer 135 controls the timing and operation of the entire mechanisms. Using valve block 136, and piping 138A, 138B, and 138C, the computer directs the following sequential operation:

1) drum 133 is filled with a bath mixture of ozonenated water (reservoir 113) with detergent (detergent reservoir 137) (note, in some embodiments, this step is broken into two components- a detergent bath followed by an ozone bath to sterilize and breakdown the detergent);

2) motor 134 causes agitator 139 to agitate the liquid mixture and contaminated fabric material within drum 133;

3) the bath and residue from drum 133 is pumped (not shown) from drum 133 to the waste disposal via waste hook-up 130B;

4) drum 133 is filled with a bath of ozonenated water from reservoir 113;

5) motor 134, via agitator 139, agitates the contents of drum 133;

6) drum 133 is emptied of all liquid and residue.

In one embodiment of the invention, drum 133 is chilled to extend the life of ozone therein and thereby obtain an enhanced sterilizing operation. Additionally, in another embodiment, drum 133 is spun to help dislodge liquid from the fabrics within drum 133.

In this manner, the contaminated fabrics are cleaned and sterilized permitting the now sterilized fabrics to be disposed in any traditional means and even to be susceptible for reuse.

Note that the operator of the mechanism is not required to touch, handle, or physically move the contaminated material except while it is contained with the drum. The risk to the operator of becoming ill due to the is reduced to a bare minimum.

It is clear from the foregoing that the present invention provides for new and improved cleaning and sterilization mechanism, and involves the use of numerous inventions.

What is claimed is:

1. An ozonenating system comprising:
   a) a pressure vessel having a selected liquid therein;
   b) means for injecting pressurized ozone gas into the liquid within said pressure vessel;
   c) a container having an article therein;
   d) means for communicating a mixture of liquid and ozone gas from said pressure vessel to said container such that said mixture contacts said article;
   e) means for removing excess mixture from said container; and,
   f) means for chilling said container and aid pressure vessel.

2. The ozonenating system according to claim 1 wherein said means for removing excess mixture communicates said excess mixture to an ozone destruct mechanism.

3. The ozonenating system according to claim 1 wherein said means for removing excess mixture communicates with a waste water disposal system.

4. The ozonenating system according to claim 1 further including means for diffusing said ozone gas in said selected liquid in said pressure vessel.

5. The ozonenating system according to claim 4 wherein said liquid is distilled water.

6. The ozonenating system according to claim 5 further including:
   a) first valve means for disengaging said container from said pressurized vessel; and,
   b) second valve means for disengaging said container from said means for destruct.

7. The ozonenating system according to claim 6 wherein said first and said second valve means seal upon disengagement.

8. The ozonenating system according to claim 7 wherein said first valve means is opened by a selected amount of pressure from said pressure vessel.

9. The ozonenating system according to claim 7 wherein said second valve means includes means for regulating an outflow rate so as to maintain a selected amount of pressure from said container.

10. The ozonenating system according to claim 7 wherein said article within said container includes a hollow tube having at least N openings and further including an adapter means communicating mixture from said pressure vessel via said first valve to N-1 of said N openings in said hollow tube.

11. An ozone bath generating system comprising:
a) a pressure vessel having a selected liquid material therein;
b) means for injecting pressurized ozone gas into the liquid material within said pressure vessel;
c) means for chilling said pressure vessel; and,
d) a container having an article therein;
e) means for communicating a mixture of liquid material and ozone gas from said pressure vessel to said container;
f) means for removing excess mixture from said container;
g) a first valve means for disengaging said container from said pressure vessel, said first valve sealing upon disengagement; and,
h) a second valve means for disengaging said container from said means for removing excess mixture, said second valve means sealing upon disengagement.

12. The ozone bath generating system according to claim 11 further including means for destroying ozone in said excess mixture.

13. The ozone bath generating system according to claim 12 wherein said means for removing excess mixture communicates with a waste water disposal system.

14. The ozone bath generating system according to claim 11 further including means for diffusing said ozone gas in said liquid material in said pressure vessel.

15. The ozone bath generating system according to claim 14 wherein said liquid material is distilled water.

16. The ozone bath generating system according to claim 11 wherein said first valve means is opened by a selected amount of pressure from said pressure vessel.

17. The ozone bath generating system according to claim 11 wherein said second valve means is opened by a selected amount of pressure from said container.

18. The ozone bath generating system according to claim 11 wherein said article within said container includes a hollow article having at least N openings and further including an adapter means communicating mixture from said pressure vessel via said first valve to N−1 of said N openings in said article tube.

19. An sterilizing system comprising:
a) a pressure vessel having a selected liquid material therein;
b) means for injecting pressurized ozone gas into the liquid material within said pressure vessel;
c) a container having an article therein;
d) means for communicating said mixture of liquid material and ozone gas from said pressure vessel to said container;
e) means for removing excess mixture from said container; and,
f) means for chilling said container and said pressure vessel.

20. The sterilizing system according to claim 19 further including means for destroying ozone in said excess mixture from said container.

21. The sterilizing system according to claim 19 wherein said means for removing excess mixture communicates with a waste water disposal system.

22. The sterilizing system according to claim 19 further including means for diffusing said ozone gas in said liquid material within said pressure vessel.

23. The sterilizing system according to claim 22 wherein said liquid material is distilled water.

24. The sterilizing system according to claim 23 further including:
a) first valve means for disengaging said container from said pressurized vessel; and,
b) second valve means for disengaging said container from said means for destruct.

25. The sterilizing system according to claim 24 wherein said first and said second valve means seal upon disengagement.

26. The sterilizing system according to claim 25 wherein said first valve means is opened by a selected amount of pressure from said pressure vessel.

27. The sterilizing system according to claim 25 wherein said second valve means is opened by a selected amount of pressure from said container.

28. The sterilizing system according to claim 25 wherein said article within said container includes a hollow tube having at least N openings and further including an adapter means communicating mixture from said pressure vessel via said first valve to N-1 of said N openings in said hollow tube.

* * * * *